United States Patent
Goryshin et al.

(10) Patent No.: US 9,238,671 B2
(45) Date of Patent: Jan. 19, 2016

(54) OLIGONUCLEOTIDE REPLACEMENT FOR DI-TAGGED AND DIRECTIONAL LIBRARIES

(75) Inventors: Igor Goryshin, San Diego, CA (US); Bradley Baas, San Diego, CA (US); Ramesh Vaidyanathan, San Diego, CA (US); Mark Maffitt, Madison, WI (US)

(73) Assignee: ILLUMINA, INC., San Diego, CA (US)

( * ) Notice: Subject to any disclaimer, the term of this patent is extended or adjusted under 35 U.S.C. 154(b) by 288 days.

(21) Appl. No.: 13/979,346

(22) PCT Filed: Jan. 30, 2012

(86) PCT No.: PCT/US2012/023139
§ 371 (c)(1),
(2), (4) Date: Oct. 13, 2013

(87) PCT Pub. No.: WO2012/103545
PCT Pub. Date: Aug. 2, 2012

(65) Prior Publication Data
US 2014/0031261 A1  Jan. 30, 2014

Related U.S. Application Data

(60) Provisional application No. 61/437,451, filed on Jan. 28, 2011, provisional application No. 61/506,777, filed on Jul. 12, 2011.

(51) Int. Cl.
C12P 19/34 (2006.01)
C12N 9/12 (2006.01)
C40B 50/06 (2006.01)
C07H 21/00 (2006.01)
C12N 15/10 (2006.01)
C12Q 1/68 (2006.01)

(52) U.S. Cl.
CPC .............. *C07H 21/00* (2013.01); *C12N 9/1241* (2013.01); *C12N 15/1065* (2013.01); *C12N 15/1093* (2013.01); *C12P 19/34* (2013.01); *C12Q 1/6855* (2013.01); *C40B 50/06* (2013.01)

(58) Field of Classification Search
None
See application file for complete search history.

(56) References Cited

U.S. PATENT DOCUMENTS 5,925,545 A   7/1999 Reznikoff et al.
2010/0120098 A1   5/2010 Grunenwald et al.

OTHER PUBLICATIONS

Albert et al., "Simple, Sensitive, and Specific Detection of Human Immunodeficiency Virus Type 1 in Clinical Specimens by Polymerase Chain Reaction with Nested Primers," J. Clin. Microbiol. 1990, 28:1560-1564.*
Australian Patent Examination Report for application No. 2012211081 mailed Feb. 11, 2015.
Adey, , "Rapid, low-input, low-bias construction of shotgun fragment libraries by high-density in vitro transposition", Genome Biology 11 r119, Dec. 8, 2010, 47 pages.
Caruccio, Nicholas , "Preparation of next-generation sequencing libraries using Nextera(TM) technology: simultaneous DNA fragmentation and adaptor tagging by in vitro transposition", Methods in Molecular Biology, 733, 2011, 241-255.
Gertz, Jason et al., "Transposease mediated construction of RNA-seq libraries", Genome Research, 22 (1), 2012, 134-141.
Syed, Fraz et al., "Optimized library preparation method for next-generation sequencing", Nature Methods, 6(10), 2009, I-II.

* cited by examiner

*Primary Examiner* — Samuel Woolwine
*Assistant Examiner* — Kaijiang Zhang
(74) *Attorney, Agent, or Firm* — Kajal Chowdhury; Illumina, Inc.

(57) ABSTRACT

Transposomes and oligonucleotide replacement methods to make DNA libraries that have distinct 5' and 3' tags, and to make directional libraries that are enriched for a desired strand.

13 Claims, 5 Drawing Sheets

```
                    Transposon End 1
      5'  AGATGTGTATAAGAGACAG  3'
          ||||||||||||||||||||
          TCTACACATATTCTCTGTC  5'   19 bases 3'
           CTACACATATTCTCTGTC  5'   18 bases 3'
            TACACATATTCTCTGTC  5'   17 bases 3'
             ACACATATTCTCTGTC  5'   16 bases 3'
              CACATATTCTCTGTC  5'   15 bases 3'
               ACATATTCTCTGTC  5'   14 bases 3'
                CATATTCTCTGTC  5'   13 bases 3'
                 ATATTCTCTGTC  5'   12 bases 3'
                  TATTCTCTGTC  5'   11 bases 3'
                   ATTCTCTGTC  5'   10 bases 3'
                    TTCTCTGTC  5'    9 bases 3'
                     TCTCTGTC  5'    8 bases 3'
```

Arbitrary Tag 1 (5' end)

Non-Transferred Strand Deletions

Fig. 3

OLIGONUCLEOTIDE REPLACEMENT FOR DI-TAGGED AND DIRECTIONAL LIBRARIES

RELATED APPLICATIONS

This application claims the benefit of priority to U.S. provisional application Ser. 61/437,451, filed Jan. 28, 2011, and Ser. 61/506,777, filed Jul. 12, 2011, both entitled "Fragmenting and Di-Tagging DNA using a transposon with oligonucleotide replacement, non-displacement gap-fill, and ligation. The contents of these applications are incorporated herein by reference in their entirety.

FIELD OF THE INVENTION

The present invention relates to molecular biology, and more specifically to methods of using transposases to fragment and tag nucleic acids, which can be useful as DNA libraries for sequencing.

BACKGROUND OF THE INVENTION

Sample preparation for next-generation sequencing can involve fragmentation of genomic DNA or double-stranded cDNA (prepared from RNA) into smaller fragments, followed by addition of functional tag sequences ("tags") to the strands of the fragments. Where a single-stranded sequence is tagged at both ends, the term "di-tagged" can be used. Such tags include priming sites for DNA polymerases for sequencing reactions, restriction sites, and domains for capture, amplification, detection, address, and transcription promoters. Previous methods for generating DNA fragment libraries required fragmenting the target DNA mechanically using a sonicator, nebulizer, or by a nuclease, and then joining (e.g., by ligation) the oligonucleotides containing the tags to the ends of the fragments.

A novel method for using transposons to rapidly achieve these steps was disclosed in US 2010/0120098 by Grunenwald, which is incorporated herein by reference, to generate fragments from any double-stranded DNA (e.g. genomic, amplicon, viral, phage, cDNA derived from RNA, etc.). Particularly useful transposon systems include the hyperactive Tn5 transposon system described in U.S. Pat. No. 5,965,443 and U.S. Pat. No. 6,437,109 by Reznikoff, and the Mu transposon system in U.S. Pat. No. 6,593,113 by Tenkanen, all of which are incorporated herein by reference. Reznikoff in particular described a 19-base transposase end sequence (SEQ ID NO:3) that is frequently referred to as "ME". In some embodiments of the transposon method, polymerase chain reaction (PCR) is used as a downstream step for DNA amplification. This can raise concerns because of PCR's potential to over- or underrepresent the relative amounts of a given sequence, depending on its G+C composition, especially in regions of extreme G+C content where PCR bias can confound the annotation and analysis of the data.

SUMMARY OF THE INVENTION

The present invention provides a method for adding one or more tags to the double-stranded product of a tagmentation reaction. The method involves providing a double-stranded target nucleic acid and a transposome having a transposase with two transposon end sequences: a "transferred strand" and a "non-transferred strand". The transposome breaks the target nucleic acid into fragments while covalently transferring the transferred strand to a first strand of the fragment; the non-transferred strand of the transposome remains hybridized to the transferred strand. In one embodiment, the non-transferred strand has the general formulas $$BTGTYTCBTN_{1-9} \quad \text{SEQ ID NO: 20}$$

$$NTGTMTCNTN_{0-10} \quad \text{SEQ ID NO: 21}$$

where the IUPAC nomenclature for degenerate nucleotide positions is used, and $N_{x-y}$ indicates a sequence having a range of x to y nucleotides, inclusive. Among the fragments, the non-transferred strand is removed from the transferred strand and replaced by an oligo that comprises a tag sequence. The replacement oligo is then joined to the second strand of the fragment by ligation and optionally by an extension step. The result of the method is a fragment of the target nucleic acid that has been tagged with one or more tag sequences, which can be useful for subsequent analysis, such as sequencing.

The invention also provides a method for generating directional libraries by providing the target nucleic acid where one strand is chemically modified. Selectively enriching one strand in the product of the tagementation reaction results in a fragment that has been tagged in a strand-specific manner, i.e. a 5'-end tag and a 3'-end tag.

Novel transposase end sequences are also provided herein, having the general sequences $$MRWTGTGHWKAVGARACAV \quad \text{SEQ ID NO: 1}$$

and $$NSHBGHSHDDRNGAKACAN. \quad \text{SEQ ID NO: 2}$$

These end sequences can be used in the methods of the invention, and with transposases for related tagmentation reactions in general.

BRIEF DESCRIPTION OF THE DRAWINGS

FIG. 3 shows various alternate versions of the non-transferred strands. At the top, the 19-base ME transferred end (SEQ ID NO:3) with an attached tag sequence is shown for reference Immediately below, the 19-base complementary non-transferred end is shown as SEQ ID NO:19 in 3'-to-5' orientation. As disclosed herein, however, a non-transferred end can also be truncated by deletions into versions with 18 bases (SEQ ID NO:18), 17 bases (SEQ ID NO:17), 16 bases (SEQ ID NO:16), 15 bases (SEQ ID NO:15), 14 bases (SEQ ID NO:14), 13 bases (SEQ ID NO:13), 12 bases (SEQ ID NO:12), 11 bases (SEQ ID NO:11), 10 bases (SEQ ID NO:10), 9 bases (SEQ ID NO:9), or 8 bases (SEQ ID NO:8).

DETAILED DESCRIPTION

Figure 1:
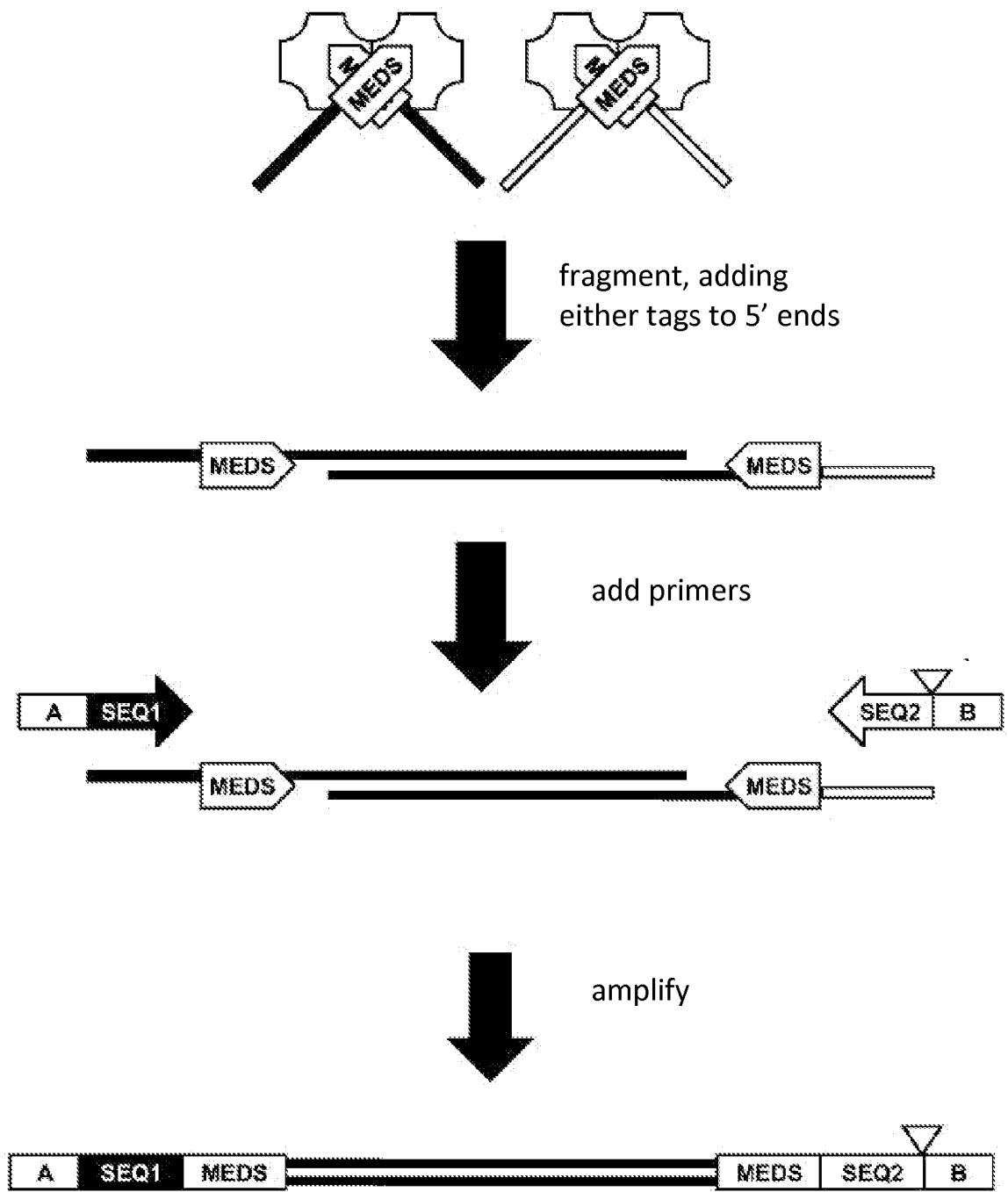
FIG. 1 provides a schematic illustration of a tagmentation reaction. The squares with engrailed corners represent transposases, for example Tn5 or Mu transposases. The MEDS refers to a double-stranded ME ("mosaic end"), exemplified by a Tn5 transposase end sequence, such as SEQ ID NO:3 hybridized to SEQ ID NO:19. Attached to the MEDS are arbitrary tags, shown here as light or dark bars. Together, the squares, MEDS, and tags depict a transposome, which can be used to fragment a target nucleic acid. A double-stranded fragmentation product is shown as parallel dark bars, with certain attached sequences, as discussed below. The SEQ1 and SEQ2 refer to sequences complementary to the arbitrary tags, which can be part of primers used for PCR, for example. The inverted triangle represents an optional insertion point for additional tag sequences, such as a bar code. A and B represent additional sequences that can be attached via PCR. As shown, the transposomes can be used to fragment a target nucleic acid to generate double-stranded fragments having sequences at both ends, which can be useful for bar-coding and sequencing.
Figure 2A:
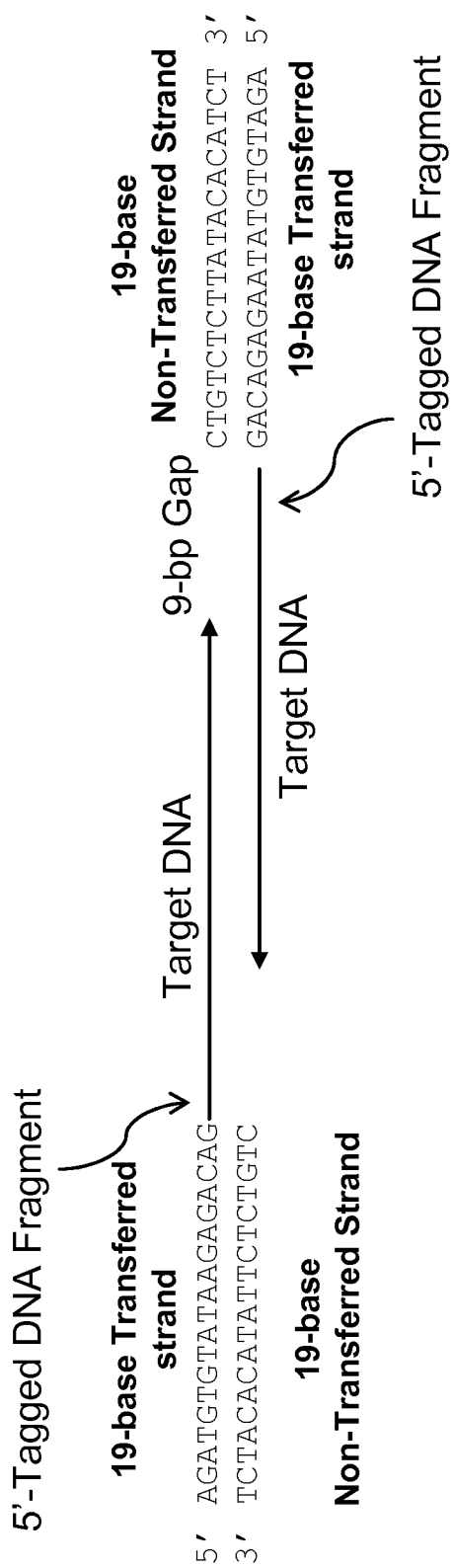
FIG. 2a provides a more detailed geometry of the tagmentation product of the second row in FIG. 1. As shown, the tagmentation reaction results in fragmented target DNA where the 5' end of the upper strand is covalently attached to a 19-base "transferred strand" (SEQ ID NO:3). The 5' end of the lower strand is similarly attached to another copy of the transferred strand, shown in 3'-to-5' orientation (SEQ ID NO:3). However, the tagmentation leaves a 9-base single-stranded gap between the 3' end of the target fragment and the 5' end of the other (non-transferred) strand of the transposome. Because this strand does not become covalently attached to the 3' ends of the target nucleic acid fragment, it is described as a "non-transferred end" (SEQ ID NO:19), although the non-transferred end remains associated with the fragment by hybridization to the transferred strand.
Figure 2B:
FIG. 2b shows the same tagmentation product as in FIG. 2a, but using the schematic form used in the other figures. For ease of illustration, the tags have been omitted from FIG. 2a and FIG. 2b.

The present invention provides an improved method for preparing di-tagged dsDNA. The method involves (a) providing a double-stranded target nucleic acid and a transposome having a transposase with two transposon end sequences: a "transferred strand" and a "non-transferred strand"; (b) allowing the transposome to fragment the target nucleic acid, whereby the transferred strand is covalently transferred to a first strand of the fragment, and the non-transferred strand remains hybridized to the transferred strand; (c) removing the non-transferred strand from the transferred strand; (d) providing a replacement oligo that comprises a tag sequence, to hybridize to transferred strand; and (e) ligating the replacement oligo to the second strand of the fragment. Thus, the method generates a tagmentation product having a transferred strand and a replacement oligo.

The target DNA used in the method can be any nucleic acid of interest. Target nucleic acids can include DNA, peptide nucleic acid, morpholino nucleic acid, locked nucleic acid, glycol nucleic acid, threose nucleic acid, mixtures thereof, and hybrids thereof. In a preferred embodiment, genomic DNA fragments or amplified copies thereof are used as the target nucleic acid. In another preferred embodiment, mitochondrial or chloroplast DNA is used.

A target nucleic acid can comprise any nucleotide sequence. In some embodiments, the target nucleic acid comprises homopolymer sequences. A target nucleic acid can also include repeat sequences. Repeat sequences can be any of a variety of lengths including, for example, 2, 5, 10, 20, 30, 40, 50, 100, 250, 500, 1000 nucleotides or more. Repeat sequences can be repeated, either contiguously or non-contiguously, any of a variety of times including, for example, 2, 3, 4, 5, 6, 7, 8, 9, 10, 15, 20 times or more.

Some embodiments described herein can utilize a single target nucleic acid. Other embodiments can utilize a plurality of target nucleic acids. In such embodiments, a plurality of target nucleic acids can include a plurality of the same target nucleic acids, a plurality of different target nucleic acids where some target nucleic acids are the same, or a plurality of target nucleic acids where all target nucleic acids are different. Embodiments that utilize a plurality of target nucleic acids can be carried out in multiplex formats so that reagents are delivered simultaneously to the target nucleic acids, for example, in one or more chambers or on an array surface. In some embodiments, the plurality of target nucleic acids can include substantially all of a particular organism's genome. The plurality of target nucleic acids can include at least a portion of a particular organism's genome including, for example, at least about 1%, 5%, 10%, 25%, 50%, 75%, 80%, 85%, 90%, 95%, or 99% of the genome. In particular embodiments the portion can have an upper limit that is at most about 1%, 5%, 10%, 25%, 50%, 75%, 80%, 85%, 90%, 95%, or 99% of the genome Target nucleic acids can be obtained from any source. For example, target nucleic acids may be prepared from nucleic acid molecules obtained from a single organism or from populations of nucleic acid molecules obtained from natural sources that include one or more organisms. Sources of nucleic acid molecules include, but are not limited to, organelles, cells, tissues, organs, or organisms. Cells that may be used as sources of target nucleic acid molecules may be prokaryotic (bacterial cells, for example, *Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium,* and *Streptomyces* genera); archeaon, such as crenarchaeota, nanoarchaeota or euryarchaeotia; or eukaryotic such as fungi, (for example, yeasts), plants, protozoans and other parasites, and animals (including insects (for example, *Drosophila* spp.), nematodes (e.g., *Caenorhabditis elegans*), and mammals (for example, rat, mouse, monkey, non-human primate and human).

In some embodiments, the target nucleic acid can be provided where one strand is chemically modified, such as with a fragmentation site. A fragmentation site can be used to cleave the physical, but not the informational association between a first barcode sequence and a second barcode sequence. Cleavage may be by biochemical, chemical or other means. In some embodiments, a fragmentation site can include a nucleotide or nucleotide sequence that may be fragmented by various means. For example, a fragmentation site may be a substrate for an enzyme, such as a nuclease, that will cleave the physical association between a first barcode sequence and a second barcode sequence. For example, the fragmentation site comprises a restriction endonuclease site and may be cleaved with an appropriate restriction endonuclease. In another example, a fragmentation site can comprise at least one ribonucleotide in a nucleic acid that may otherwise comprise deoxyribonucleotides and may be cleaved with an RNAse. Chemical cleavage agents capable of selectively cleaving the phosphodiester bond between a deoxyribonucleotide and a ribonucleotide include metal ions, for example rare-earth metal ions (e.g., $La^{3+}$, particularly $Tm^{3+}$, $Yb^{3+}$ or $Lu^{3+}$ (Chen et al. Biotechniques. 2002, 32: 518-520; Komiyama et al. Chem. Commun. 1999, 1443-1451)), Fe(3) or Cu(3), or exposure to elevated pH, e.g., treatment with a base such as sodium hydroxide. As used herein, selective cleavage of the phosphodiester bond between a deoxyribonucleotide and a ribonucleotide can refer to the chemical cleavage agent is not capable of cleaving the phosphodiester bond between two deoxyribonucleotides under the same conditions.

In another example, the fragmentation site can comprise one or more recognition sequences for a nickase, that is, a nicking endonuclease that breaks one strand of a double-stranded nucleic acid. Thus, the fragmentation site can comprise a first nickase recognition sequence, a second nickase recognition sequence. The cut site for each recognition sequence can be the same site or different site.

In another example, a fragmentation site can include one or more nucleotide analogues that comprise an abasic site and permits cleavage at the fragmentation site in the presence of certain chemical agents, such as polyamine, N,N'-dimethyl-ethylene-diamine (DMED) (U.S. Patent Publication No. 2010/0022403). In one embodiment, the chemical modification can be a conversion of cytosines to uracils. In some embodiments, an abasic site may be created within a fragmentation site by first providing a fragmentation site comprising a deoxyuridine (U) of a double stranded nucleic acid. The enzyme uracil DNA glycosylase (UDG) may then be used to remove the uracil base, generating an abasic site on one strand. The polynucleotide strand including the abasic site may then be cleaved at the abasic site by treatment with endonuclease (e.g. Endo IV endonuclease, AP lyase, FPG glycosylase/AP lyase, Endo VIII glycosylase/AP lyase), heat or alkali. Abasic sites may also be generated at nucleotide analogues other than deoxyuridine and cleaved in an analogous manner by treatment with endonuclease, heat or alkali. For example, 8-oxo-guanine can be converted to an abasic site by exposure to FPG glycosylase. Deoxyinosine can be converted to an abasic site by exposure to AlkA glycosylase. The abasic sites thus generated may then be cleaved, typically by treatment with a suitable endonuclease (e.g. Endo IV, AP lyase). (U.S. Patent Publication No. 2011/0014657).

In another example, a fragmentation site may include a diol linkage which permits cleavage by treatment with periodate (e.g., sodium periodate). In another example, a fragmentation site may include a disulphide group which permits cleavage with a chemical reducing agent, e.g. Tris(2-carboxyethyl)-phosphate hydrochloride (TCEP).

In some embodiments, a fragmentation site may include a cleavable moiety that may be subject to photochemical cleavage. Photochemical cleavage encompasses any method which utilizes light energy in order to achieve cleavage of nucleic acids, for example, one or both strands of a double-stranded nucleic acid molecule. A site for photochemical cleavage can be provided by a non-nucleotide chemical moiety in a nucleic acid, such as phosphoramidite [4-(4,4'-dimethoxytrityloxy)butyramidomethyl)-1-(2-nitrophenyl)-ethyl]-2-cyanoethyl-(N,N-diisopropyl)-phosphoramidite) (Glen Research, Sterling, Va., USA, Cat No. 10-4913-XX).

In some embodiments, a fragmentation site can include a peptide, for example, conjugate structure in which a peptide molecule is linked to a nucleic acid. The peptide molecule can subsequently be cleaved by a peptidase enzyme of the appropriate specificity, or any other suitable means of non-enzymatic chemical or photochemical cleavage. In some embodiments, a conjugate between peptide and nucleic acid will be formed by covalently linking a peptide to a nucleic acid, e.g., a strand of a double-stranded nucleic acid. Conjugates between a peptide and nucleic acid can be prepared using techniques generally known in the art. In one such technique the peptide and nucleic acid components of the desired amino acid and nucleotide sequence can be synthesized separately, e.g. by standard automated chemical synthesis techniques, and then conjugated in aqueous/organic solution. By way of example, the OPeC™ system commercially available from Glen Research is based on the native ligation of an N-terminal thioester-functionalized peptide to a 5'-cysteinyl oligonucleotide.

The method of the invention can use any transposase that can accept a transposase end sequence and fragment a target nucleic acid, attaching a transferred end, but not a non-transferred end. A "transposome" is comprised of at least a transposase enzyme and a transposase recognition site. In some such systems, termed "transposomes", the transposase can form a functional complex with a transposon recognition site that is capable of catalyzing a transposition reaction. The transposase or integrase may bind to the transposase recognition site and insert the transposase recognition site into a target nucleic acid in a process sometimes termed "tagmentation". In some such insertion events, one strand of the transposase recognition site may be transferred into the target nucleic acid.

Some embodiments can include the use of a hyperactive Tn5 transposase and a Tn5-type transposase recognition site (Goryshin and Reznikoff, *J. Biol. Chem.*, 273:7367 (1998)), or MuA transposase and a Mu transposase recognition site comprising R1 and R2 end sequences (Mizuuchi, K., *Cell*, 35: 785, 1983; Savilahti, H, et al., *EMBO J.*, 14: 4893, 1995). An exemplary transposase recognition site that forms a complex with a hyperactive Tn5 transposase (e.g., EZ-Tn5™ Transposase, Epicentre Biotechnologies, Madison, Wis.).

More examples of transposition systems that can be used with certain embodiments provided herein include *Staphylococcus aureus* Tn552 (Colegio et al., *J. Bacteriol.*, 183: 2384-8, 2001; Kirby C et al., *Mol. Microbiol.*, 43: 173-86, 2002), Ty1 (Devine & Boeke, *Nucleic Acids Res.*, 22: 3765-72, 1994 and International Publication WO 95/23875), Transposon Tn7 (Craig, N L, *Science*. 271: 1512, 1996; Craig, N L, Review in: *Curr Top Microbiol Immunol.*, 204:27-48, 1996), Tn/O and IS10 (Kleckner N, et al., *Curr Top Microbiol Immunol.*, 204:49-82, 1996), Mariner transposase (Lampe D J, et al., *EMBO J.*, 15: 5470-9, 1996), Tc1 (Plasterk R H, *Curr. Topics Microbiol. Immunol.*, 204: 125-43, 1996), P Element (Gloor, G B, *Methods Mol. Biol.*, 260: 97-114, 2004), Tn3 (Ichikawa & Ohtsubo, *J Biol. Chem.* 265:18829-32, 1990), bacterial insertion sequences (Ohtsubo & Sekine, *Curr. Top. Microbiol. Immunol.* 204: 1-26, 1996), retroviruses (Brown, et al., *Proc Natl Acad Sci USA,* 86:2525-9, 1989), and retrotransposon of yeast (Boeke & Corces, *Annu Rev Microbiol.* 43:403-34, 1989). More examples include IS5, Tn10, Tn903, IS911, and engineered versions of transposase family enzymes (Zhang et al., (2009) *PLoS Genet.* 5:e1000689. Epub 2009 Oct. 16; Wilson C. et al (2007) *J. Microbiol. Methods* 71:332-5).

The Tn5 system uses Tn5 transposases with the 19-base ME sequence (SEQ ID NO:3) as the transferred end. As discussed in Example 2, however, other transferred ends can be used, and can be described by the generic formulas

MRWTGTGHWKAVGARACAV SEQ ID NO: 1 and

NSHBGHSHDDRNGAKACAN. SEQ ID NO: 2

More particularly, the transferred ends can be

CGTTGTGTGGACGAGACAC 11G:C(C1) SEQ ID NO: 4

CGTTGTGTGGACGAGACAG 11G:C(G1) SEQ ID NO: 5

AGATGTGCATATGATACAG Diff1(G1) SEQ ID NO: 6

AG.TGT....AAGAGACAT Shorty SEQ ID NO: 7

TGACGCGGGTAAGAGACAA Malt 1 SEQ ID NO: 22

GGATGCGATGAGGAGACAA Malt 6 SEQ ID NO: 23

ACATGACCAAGAGAGACAG Malt 8 SEQ ID NO: 24

AGCGGTGAATAAGAGACAA Malt 10 SEQ ID NO: 25

AGCGGTGAATAAGAGACAG Malt 11, SEQ ID NO: 26 or

ACATGAGTATAAGAGACAA Malt 12. SEQ ID NO: 27

Based on the truncated sequences discussed in Example 1 and the complementary sequences to SEQ ID NO:1 and SEQ ID NO:2, the present invention also provides a non-transferred strands having the general formula:

BTGTYTCBTN$_{1-10}$ SEQ ID NO: 20

NTGTMTCNTN$_{0-10}$ SEQ ID NO: 21 where the N$_{0-10}$ indicates zero to ten nucleotides. As examples, the non-transferred strand can be selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18.

The end sequences can further comprise a tag sequence, which can be added covalently to the fragments in the process of the tagmentation method. As used herein, the term "tag" means a nucleotide sequence that is attached to another nucleic acid to provide the nucleic acid with some functionality. Examples of tags include barcodes, primer sites, affinity tags, and reporter moieties.

Generally, a barcode can include one or more nucleotide sequences that can be used to identify one or more particular nucleic acids. The barcode can be an artificial sequence, or can be a naturally occurring sequence, such as a g-code, described herein. A barcode can comprise at least about 1, 2, 3, 4, 5, 6, 7, 8, 9, 10, 11, 12, 13, 14, 15, 16, 17, 18, 19, 20 or more consecutive nucleotides. In some embodiments, a barcode comprises at least about 10, 20, 30, 40, 50, 60, 70 80, 90, 100 or more consecutive nucleotides. In some embodiments, at least a portion of the barcodes in a population of nucleic acids comprising barcodes is different. In some embodiments, at least about 10%, 20%, 30%, 40%, 50%, 60%, 70%, 80%, 90%, 95%, 99% of the barcodes are different. In more such embodiments, all of the barcodes are different. The diversity of different barcodes in a population of nucleic acids comprising barcodes can be randomly generated or non-randomly generated.

In some embodiments, a transposon sequence comprises at least one barcode. In some embodiments, a transposon sequence comprises a barcode comprising a first barcode sequence and a second barcode sequence. In some such embodiments, the first barcode sequence can be identified or designated to be paired with the second barcode sequence. For example, a known first barcode sequence can be known to be paired with a known second barcode sequence using a reference table comprising a plurality of first and second barcode sequences known to be paired to one another.

In another example, the first barcode sequence can comprise the same sequence as the second barcode sequence. In another example, the first barcode sequence can comprise the reverse complement of the second barcode sequence. In some embodiments, the first barcode sequence and the second barcode sequence are different ("bi-codes"). It will be understood that in some embodiments, the vast number of available barcodes permits each template nucleic acid molecule to comprise a unique identification. Unique identification of each molecule in a mixture of template nucleic acids can be used in several applications to identify individual nucleic acid molecules, in samples having multiple chromosomes, genomes, cells, cell types, cell disease states, and species, for example in haplotype sequencing, parental allele discrimination, metagenomic sequencing, and sample sequencing of a genome.

In some embodiments, useful tag is a primer site that can hybridize to a primer. The orientation of the primer sites in such embodiments can be such that a primer hybridizing to the first primer site and a primer hybridizing to the second primer site are in the same orientation, or in different orientations. In one embodiment, the primer sequence can be complementary to a primer used for amplification. In another embodiment, the primer sequence is complementary to a primer used for sequencing.

In some embodiments, a tag can include a first primer site, a second primer site having a non-amplifiable site disposed therebetween. The non-amplifiable site is useful to block extension of a polynucleotide strand between the first and second primer sites, wherein the polynucleotide strand hybridizes to one of the primer sites. The non-amplifiable site can also be useful to prevent concatamers. Examples of non-amplifiable sites include a nucleotide analogue, non-nucleotide chemical moiety, amino-acid, peptide, and polypeptide. In some embodiments, a non-amplifiable site comprises a nucleotide analogue that does not significantly base-pair with A, C, G or T.

In some embodiments, a tag can be an affinity tag. Affinity tags can be useful for the bulk separation of target nucleic acids hybridized to hybridization tags. As used herein, the term "affinity tag" and grammatical equivalents can refer to a component of a multi-component complex, wherein the components of the multi-component complex specifically interact with or bind to each other. For example an affinity tag can include biotin or His that can bind streptavidin or nickel, respectively. Other examples of multiple-component affinity tag complexes include, ligands and their receptors, for example, avidin-biotin, streptavidin-biotin, and derivatives of biotin, streptavidin, or avidin, including, but not limited to, 2-iminobiotin, desthiobiotin, NeutrAvidin (Molecular Probes, Eugene, Oreg.), CaptAvidin (Molecular Probes), and the like; binding proteins/peptides, including maltose-maltose binding protein (MBP), calcium-calcium binding protein/peptide (CBP); antigen-antibody, including epitope tags, and their corresponding anti-epitope antibodies; haptens, for example, dinitrophenyl and digoxigenin, and their corresponding antibodies; aptamers and their corresponding targets; poly-His tags (e.g., penta-His and hexa-His) and their binding partners including corresponding immobilized metal ion affinity chromatography (IMAC) materials and anti-poly-His antibodies; fluorophores and anti-fluorophore antibodies; and the like. In some embodiments, a tag can comprise a reporter moiety. As used herein, the term "reporter moiety" and grammatical equivalents can refer to any identifiable tag, label, or group. The skilled artisan will appreciate that many different species of reporter moieties can be used with the methods and compositions described herein, either individually or in combination with one or more different reporter moieties. In certain embodiments, a reporter moiety can emit a signal. Examples of signals fluorescent, a chemiluminescent, a bioluminescent, a phosphorescent, a radioactive, a calorimetric, or an electrochemiluminescent signals. Example reporter moieties include fluorophores, radioisotopes, chromogens, enzymes, antigens including epitope tags, semiconductor nanocrystals such as quantum dots, heavy metals, dyes, phosphorescence groups, chemiluminescent groups, electrochemical detection moieties, binding proteins, phosphors, rare earth chelates, transition metal chelates, near-infrared dyes, electrochemiluminescence labels, and mass spectrometer compatible reporter moieties, such as mass tags, charge tags, and isotopes. More reporter moieties that may be used with the methods and compositions described herein include spectral labels such as fluorescent dyes (e.g., fluorescein isothiocyanate, Texas red, rhodamine, and the like), radiolabels (e.g., $^3$H, $^{125}$I, $^{35}$S, $^{14}$C, $^{32}$P, $^{33}$P, etc.), enzymes (e.g., horseradish peroxidase, alkaline phosphatase etc.) spectral calorimetric labels such as colloidal gold or colored glass or plastic (e.g. polystyrene, polypropylene, latex, etc.) beads; magnetic, electrical, thermal labels; and mass tags. Reporter moieties can also include enzymes (horseradish peroxidase, etc.) and magnetic particles. More reporter moieties include chromophores, phosphors and fluorescent moieties, for example, Texas red, dixogenin, biotin, 1- and 2-aminonaphthalene, p,p'-diaminostilbenes, pyrenes, quaternary phenanthridine salts, 9-aminoacridines, p,p'-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenylamine, 2-oxo-3-chromen, indole, xanthen, 7-hydroxycoumarin, phenoxazine, calicylate, strophanthidin, porphyrins, triarylmethanes and flavin. Individual fluorescent compounds which have functionalities for linking to an element desirably detected in an apparatus or assay provided herein, or which can be modified to incorporate such functionalities include, e.g., dansyl chloride; fluoresceins such as 3,6-dihydroxy-9-phenylxanthydrol; rhodamineisothiocyanate; N-phenyl 1-amino-8-sulfonatonaphthalene; N-phenyl 2-amino-6-sulfonatonaphthalene; 4-acetamido-4-isothiocyanato-stilbene-2,2'-disulfonic acid; pyrene-3-sulfonic acid; 2-toluidinonaphthalene-6-sulfonate; N-phenyl-N-methyl-2-aminoaphthalene-6-sulfonate; ethidium bromide; stebrine; auromine-0,2-(9'-anthroyl) palmitate; dansyl phosphatidylethanolamine; N,N'-dioctadecyl oxacarbocyanine: N,N'-dihexyl oxacarbocyanine; merocyanine, 4-(3'-pyrenyl)stearate; d-3-aminodesoxy-equilenin; 12-(9'-anthroyl)stearate; 2-methylanthracene; 9-vinylanthracene; 2,2'(vinylene-p-phenylene)bisbenzoxazole; p-bis (2-methyl-5-phenyl-oxazolyl))benzene; 6-dimethylamino-1, 2-benzophenazin; retinol; bis(3'-aminopyridinium) 1,10-decandiyl diiodide; sulfonaphthylhydrazone of hellibrienin; chlorotetracycline; N-(7-dimethylamino-4-methyl-2-oxo-3-chromenyl)maleimide; N-(p-(2benzimidazolyl)-phenyl)maleimide; N-(4-fluoranthyl)maleimide; bis(homovanillic acid); resazarin; 4-chloro7-nitro-2,1,3-benzooxadiazole; merocyanine 540; resorufin; rose bengal; 2,4-diphenyl-3 (2H)-furanone, fluorescent lanthanide complexes, including those of Europium and Terbium, fluorescein, rhodamine, tetramethylrhodamine, eosin, erythrosin, coumarin, methyl-coumarins, quantum dots (also referred to as "nanocrystals": see U.S. Pat. No. 6,544,732), pyrene, Malachite green, stilbene, Lucifer Yellow, Cascade Blue™, Texas Red, Cy dyes (Cy3, Cy5, etc.), Alexa Fluor® dyes, phycoerythin, bodipy, and others described in the 6th Edition of the *Molecular Probes Handbook* by Richard P. Haugland.

The invention further provides a nucleic acid comprising one or two copies of the transposase end sequences, which can be generated by performing the method of the invention. When the method is performed on a target sequence and different fragments are generated, the invention provides a library of these different nucleic acids.

The non-transferred strand with or without nuclease-protecting and/or chain-termination groups (e.g. phosphorothioate and/or dideoxy) is then dissociated from the transferred strand and a replacement oligo (which may contain additional DNA tags, as discussed above, such as a sequencing tag) is annealed to the complementary transferred strand sequence with or without nuclease-protective groups (e.g. phosphorothioates). Non-displacing nucleic-acid-modifying enzymes can be used, consisting of a DNA polymerase and a DNA ligase. The DNA polymerases and ligase are utilized to fill-in and ligate the gap between the mono-tagged DNA and replacement oligonucleotide, resulting in a piece of dsDNA with a covalently bound 5' and a 3' tag. Thus, the method of the present invention provides a novel way to create di-tagged dsDNA fragments, wherein the polymerase chain reaction is optional.

The present invention also provides an improved method for preparing a directionally tagged library. The method begins by providing DNA with a strand-specific modification, such as incorporation of a cleavable nucleotide on one particular strand, such as a chemically labile nucleotide or one containing uracil or 8-oxoguanine. Other useful modified nucleotides include 8-oxoadenine, fapy-guanine, methyl-fapy-guanine, fapy-adenine, aflatoxin $B_1$-fapy-guanine, 5-hydroxy-cytosine, 5-hydroxy-uracil, and ring-opened N-7 guanine adducts (7-methylguanine). In a particular embodiment, each strand can contain a different modification, e.g. one strand can contain uracil modifications and the other strand can contain 8-oxo-guanine modifications.

The DNA is then cleaved with a mono-tagged transposome consisting of one or more transposase molecules and two oligonucleotide sequences of DNA that are the annealed modified end (ME) DNA. An (ME) sequence in the transferred DNA strand and a non-transferred strand of DNA that may contain a 19 bp ME sequence or truncated DNA sequence. The non-transferred strand (with or without nuclease protecting and/or chain termination groups, e.g. phosphorothioate and/or dideoxy) are then dissociated from the transferred strand and a replacement oligo (which may contain additional DNA sequence such as a sequencing tag) is annealed to the complementary transferred strand sequence with or without nuclease protective groups (e.g. phosphorothioates). Non-displacing nucleic acid modifying enzymes are used consisting of a DNA polymerase (e.g. thermostable polymerases, or nonthermostable polymerases such as DNA polymerase I or Klenow fragment exo) and a DNA ligase. The DNA polymerases and ligase are utilized to fill in and ligate the gap between the mono-tagged DNA and replacement oligonucleotide resulting in a piece of dsDNA with a covalently attached 5' and a 3' tag. Alternately, an oligonucleotide can be provided to fill in the gap, followed by ligation.

Either the modified or unmodified stranded can be specifically treated to enrich or suppress its functionality. The treatment can include using an enzyme, such as uracil DNA glycosylase (UDG) aka uracil N-Glycosylase (UNG), human apurinic/apyrimidinic endonuclease (APE I), formamidopyrimidine-DNA glycosylase (FPG) a.k.a 8-oxyguanine DNA glycosylase, Endonuclease IV and kinase, Endo III, Endo VIII, hOGG1, T7 Endo I, T4 PDG and afu UDG. In another embodiment, one strand can be selectively enriched by extension using a polymerase that has a preference for naturally occurring nucleotides, rather than chemically modified nucleotides. An example of such a polymerase is a fusion of a *Pyrococcus*-like polymerase to a dsDNA-binding domain from *Sulfolobus solfataricus* (SSo7d). Thus, the method of the present invention provides a novel way to create di-tagged DNA fragments from a single predetermined strand, where no subsequent amplification is necessary.

The invention also provides a transposome comprising a transposase and a nucleic acid containing one or more end sequences. The invention further provides a method for making a transposome with the end sequences by providing a transposase and providing the transferred end sequences, and then allowing the transposase to bind to the transferred end sequence. Exemplary reaction conditions are discussed in Example 1 below. Thus the invention provides a tagmentation method comprising the steps of (a) providing target nucleic acids (b) providing the transposomes of the invention, and (c) allowing the transposomes to fragment the target nucleic acids and tag at least transposase end sequences to the ends of the fragments.

Definitions

The term "comprising" as used herein is synonymous with "including," "containing," or "characterized by," and is inclusive or open-ended and does not exclude additional, unrecited elements or method steps.

As used herein the term "at least a portion" and/or grammatical equivalents thereof can refer to any fraction of a whole amount. For example, "at least a portion" can refer to at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99%, 99.9% or 100% of a whole amount.

As used herein the term "nucleic acid" and/or "oligonucleotide" and/or grammatical equivalents thereof can refer to at least two nucleotide monomers linked together. A nucleic acid can generally contain phosphodiester bonds; however, in some embodiments, nucleic acid analogs may have other types of backbones, comprising, for example, phosphoramide (Beaucage, et al., *Tetrahedron*, 49:1925 (1993); Letsinger, *J. Org. Chem.*, 35:3800 (1970); Sprinzl, et al., *Eur. J. Biochem.*, 81:579 (1977); Letsinger, et al., *Nucl. Acids Res.*, 14:3487 (1986); Sawai, et al., Chem. Lett., 805 (1984), Letsinger, et al., *J. Am. Chem. Soc.*, 110:4470 (1988); and Pauwels, et al., *Chemica Scripta*, 26:141 (1986)), phosphorothioate (Mag, et al., *Nucleic Acids Res.*, 19:1437 (1991); and U.S. Pat. No. 5,644,048), phosphorodithioate (Briu, et al., *J. Am. Chem. Soc.*, 111:2321 (1989), O-methylphosphoroamidite linkages (see Eckstein, *Oligonucleotides and Analogues: A Practical Approach*, Oxford University Press), and peptide nucleic acid backbones and linkages (see Egholm, *J. Am. Chem. Soc.*, 114:1895 (1992); Meier, et al., *Chem. Int. Ed. Engl.*, 31:1008 (1992); Nielsen, *Nature*, 365:566 (1993); Carlsson, et al., *Nature*, 380:207 (1996)).

Other analog nucleic acids include those with positive backbones (Denpcy, et al., *Proc. Natl. Acad. Sci. USA*, 92:6097 (1995)); non-ionic backbones (U.S. Pat. Nos. 5,386,023; 5,637,684; 5,602,240; 5,216,141; and 4,469,863; Kiedrowshi, et al., Angew. Chem. Intl. Ed. English, 30:423 (1991); Letsinger, et al., *J. Am. Chem. Soc.*, 110:4470 (1988); Letsinger, et al., *Nucleosides & Nucleotides*, 13:1597 (1994); Chapters 2 and 3, *ASC Symposium Series* 580, "Carbohydrate Modifications in Antisense Research", Ed. Y. S. Sanghui and P. Dan Cook; Mesmaeker, et al., *Bioorganic & Medicinal Chem. Lett.*, 4:395 (1994); Jeffs, et al., *J. Biomolecular NMR*, 34:17 (1994); *Tetrahedron Lett.*, 37:743 (1996)) and non-ribose (U.S. Pat. No. 5,235,033 and No. 5,034,506, and Chapters 6 and 7, *ASC Symposium Series* 580, "Carbohydrate Modifications in Antisense Research", Ed. Y. S. Sanghui and P. Dan Coo). Nucleic acids may also contain one or more carbocyclic sugars (see Jenkins, et al., Chem. Soc. Rev., (1995) pp. 169 176).

Modifications of the ribose-phosphate backbone may be done to facilitate the addition of additional moieties such as labels, or to increase the stability of such molecules under certain conditions. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, for example, genomic or cDNA, RNA or a hybrid, from single cells, multiple cells, or from multiple species, as with metagenomic samples, such as from environmental samples. A nucleic acid can contain any combination of deoxyribo- and ribo-nucleotides, and any combination of bases, including uracil, adenine, thymine, cytosine, guanine, inosine, xanthanine, hypoxanthanine, isocytosine, isoguanine, and base analogs such as nitropyrrole (including 3-nitropyrrole) and nitroindole (including 5-nitroindole), etc.

In some embodiments, a nucleic acid can include at least one promiscuous base. Promiscuous bases can base-pair with more than one different type of base. In some embodiments, a promiscuous base can base-pair with at least two different types of bases and no more than three different types of bases. An example of a promiscuous base includes inosine that may pair with adenine, thymine, or cytosine. Other examples include hypoxanthine, 5-nitroindole, acylic 5-nitroindole, 4-nitropyrazole, 4-nitroimidazole and 3-nitropyrrole (Loakes et al., *Nucleic Acid Res.* 22:4039 (1994); Van Aerschot et al., *Nucleic Acid Res.* 23:4363 (1995); Nichols et al., *Nature* 369:492 (1994); Bergstrom et al., *Nucleic Acid Res.* 25:1935 (1997); Loakes et al., Nucleic Acid Res. 23:2361 (1995); Loakes et al., *J. Mol. Biol.* 270:426 (1997); and Fotin et al., *Nucleic Acid Res.* 26:1515 (1998)). Promiscuous bases that can base-pair with at least three, four or more types of bases can also be used.

As used herein, the term "nucleotide analog" and/or grammatical equivalents thereof can refer to synthetic analogs having modified nucleotide base portions, modified pentose portions, and/or modified phosphate portions, and, in the case of polynucleotides, modified internucleotide linkages, as generally described elsewhere (e.g., Scheit, Nucleotide Analogs, John Wiley, New York, 1980; Englisch, Angew. *Chem. Int. Ed. Engl.* 30:613-29, 1991; Agarwal, *Protocols for Polynucleotides and Analogs*, Humana Press, 1994; and S. Verma and F. Eckstein, *Ann. Rev. Biochem.* 67:99-134, 1998). Generally, modified phosphate portions comprise analogs of phosphate wherein the phosphorous atom is in the +5 oxidation state and one or more of the oxygen atoms is replaced with a non-oxygen moiety, e.g., sulfur. Exemplary phosphate analogs include but are not limited to phosphorothioate, phosphorodithioate, phosphoroselenoate, phosphorodiselenoate, phosphoroanilothioate, phosphoranilidate, phosphoramidate, boronophosphates, including associated counterions, e.g., $H^+$, $NH_4^+$, $Na^+$, if such counterions are present. Example modified nucleotide base portions include but are not limited to 5-methylcytosine (5mC); C-5-propynyl analogs, including but not limited to, C-5 propynyl-C and C-5 propynyl-U; 2,6-diaminopurine, also known as 2-amino adenine or 2-amino-dA); hypoxanthine, pseudouridine, 2-thiopyrimidine, isocytosine (isoC), 5-methyl isoC, and isoguanine (isoG; see, e.g., U.S. Pat. No. 5,432,272). Exemplary modified pentose portions include but are not limited to, locked nucleic acid (LNA) analogs including without limitation Bz-A-LNA, 5-Me-Bz-C-LNA, dmf-G-LNA, and T-LNA (see, e.g., *The Glen Report,* 16(2):5, 2003; Koshkin et al., *Tetrahedron* 54:3607-30, 1998), and 2'- or 3'-modifications where the 2'- or 3'-position is hydrogen, hydroxy, alkoxy (e.g., methoxy, ethoxy, allyloxy, isopropoxy, butoxy, isobutoxy and phenoxy), azido, amino, alkylamino, fluoro, chloro, or bromo. Modified internucleotide linkages include phosphate analogs, analogs having achiral and uncharged intersubunit linkages (e.g., Sterchak, E. P. et al., Organic Chem., 52:4202, 1987), and uncharged morpholino-based polymers having achiral intersubunit linkages (see, e.g., U.S. Pat. No. 5,034,506). Some internucleotide linkage analogs include morpholidate, acetal, and polyamide-linked heterocycles. In one class of nucleotide analogs, known as peptide nucleic acids, including pseudocomplementary peptide nucleic acids ("PNA"), a conventional sugar and internucleotide linkage has been replaced with a 2-aminoethylglycine amide backbone polymer (see, e.g., Nielsen et al., *Science,* 254:1497-1500, 1991; Egholm et al., *J. Am. Chem. Soc.,* 114: 1895-1897 1992; Demidov et al., *Proc. Natl. Acad. Sci.* 99:5953-58, 2002; *Peptide Nucleic Acids: Protocols and Applications,* Nielsen, ed., Horizon Bioscience, 2004).

The following Examples provide illustrative embodiments and do not in any way limit the inventions provided herein.

EXAMPLES

Example 1

Oligonucleotide Replacement

A series of hyperactive Tn5 transposomes was prepared, each with one 19-base transposon end sequence:

AGATGTGTATAAGAGACAG (ME) (SEQ ID NO: 3)

(the "transferred strand") and one of the following end sequences (the "non-transferred strand"), shown in 5'-to-3' orientation:

CTGTCTCT........... 8 base  SEQ ID NO: 8
CTGTCTCTT.......... 9 base  SEQ ID NO: 9
CTGTCTCTTA......... 10 base SEQ ID NO: 10
CTGTCTCTTAT........ 11 base SEQ ID NO: 11
CTGTCTCTTATA....... 12 base SEQ ID NO: 12
CTGTCTCTTATAC...... 13 base SEQ ID NO: 13
CTGTCTCTTATACA..... 14 base SEQ ID NO: 14
CTGTCTCTTATACAC.... 15 base SEQ ID NO: 15
CTGTCTCTTATACACA... 16 base SEQ ID NO: 16
CTGTCTCTTATACACAT.. 17 base SEQ ID NO: 17
CTGTCTCTTATACACATC. 18 base SEQ ID NO: 18
CTGTCTCTTATACACATCT 19 base SEQ ID NO: 19 (ME)

where the end sequences contained a tag sequence as depicted in FIG. 3. The transposomes were prepared in a reaction mixture of 2 μl end sequence (25 μM), phosphorylated; 2 μl Tn5 transposase at 10 U/μl, in a final volume of 50 μl having final concentrations of 33 mM Tris-acetate, pH 7.8, 10 mM magnesium acetate and 66 mM potassium acetate. Alternatively, the final concentrations in the reaction volume can be 10 mM Tris-acetate, pH 7.6, 5 mM magnesium chloride, and optionally 10% (v/v) dimethylformamide. After mixing, the reaction was incubated for 1 hour at 37° C. The reaction was stopped with 10 μl of stop solution: 15% sucrose, 66 mM EDTA, 20 mM Tris pH 8, 0.1% SDS, 0.9% Orange G (Sigma O-7252) and Proteinase K at 100 μg/mL. After addition of the stop solution, the mixture was heated to 50° C. for 10 minutes.

Tagmentation reactions were performed with the transposomes to compare the ability of transposomes having truncated non-transferred end sequences compared to the 19-base non-transferred end, serving as a positive control and no non-transferred end as a negative control. Based on gel electrophoresis analysis, the target DNA in a sample was efficiently fragmented by the transposomes having 18-base to 12-base end sequences, with less efficient fragmentation with 11-base to 9 base end sequences. The 8-base end sequence demonstrated some fragmentation, but not efficiently.

Figure 4:
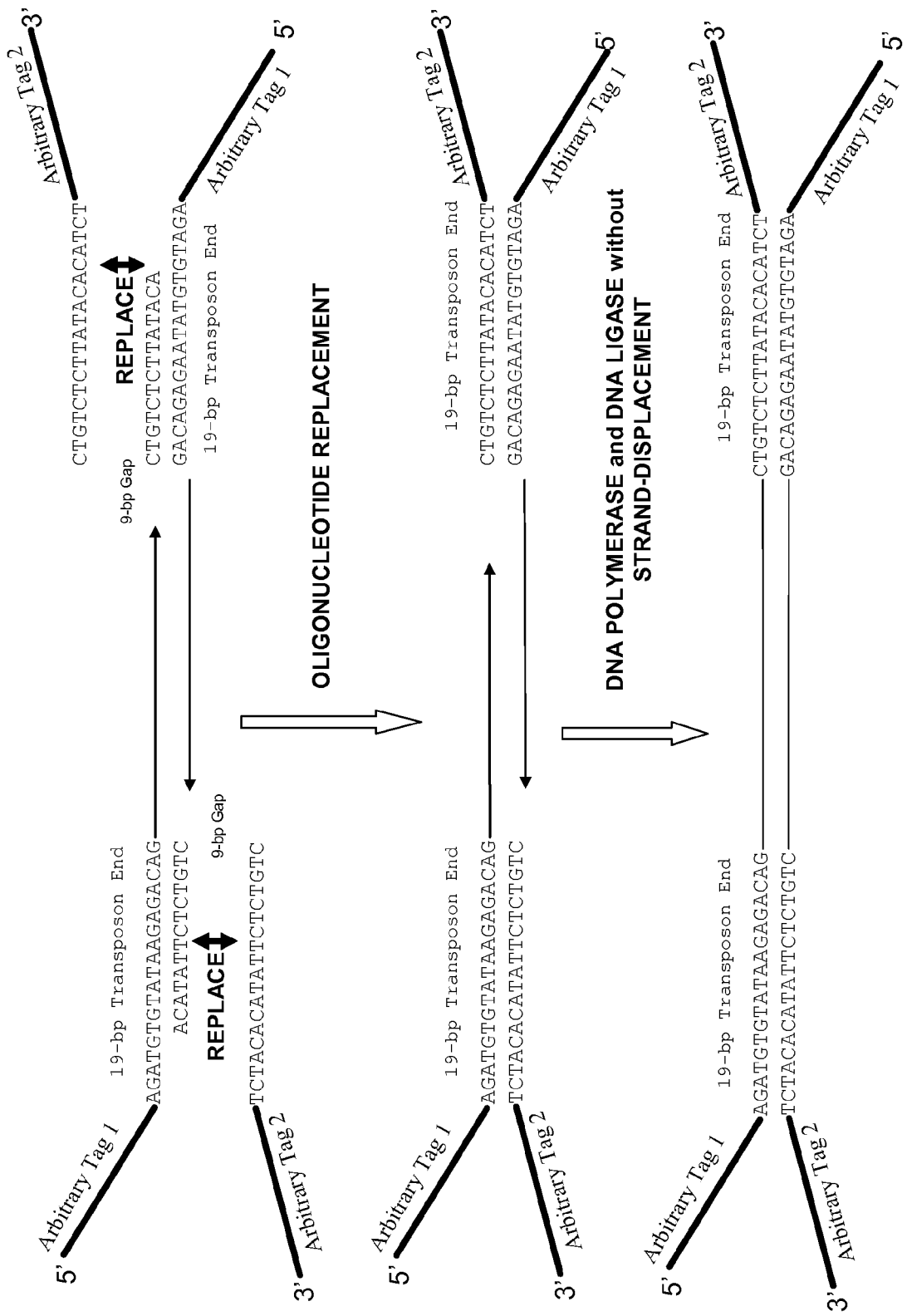
FIG. 4 illustrates an embodiment of the method of the invention, as discussed in greater detail below. The 19-bp transposon ends (transferred strand) (SEQ ID NO:3) are shown with attached Arbitrary Tag 1. An exemplary 14-base non-transferred strand (SEQ ID NO:14) is shown hybridized to a portion of the transferred strand. As shown in the top row, replacement oligonucleotides (SEQ ID NO:19) are provided (shown here attached to Arbitrary Tag 2). In the middle and bottom rows, the double-stranded 19-base transposon ends (SEQ ID NO:3, SEQ ID NO:19) are shown as attached to the target nucleic acid fragment. The product shown in the bottom row is a "di-tagged" fragment that has Arbitrary Tag 1 at the 5' end and Arbitrary Tag 2 at the 3' end.
Figure 5:
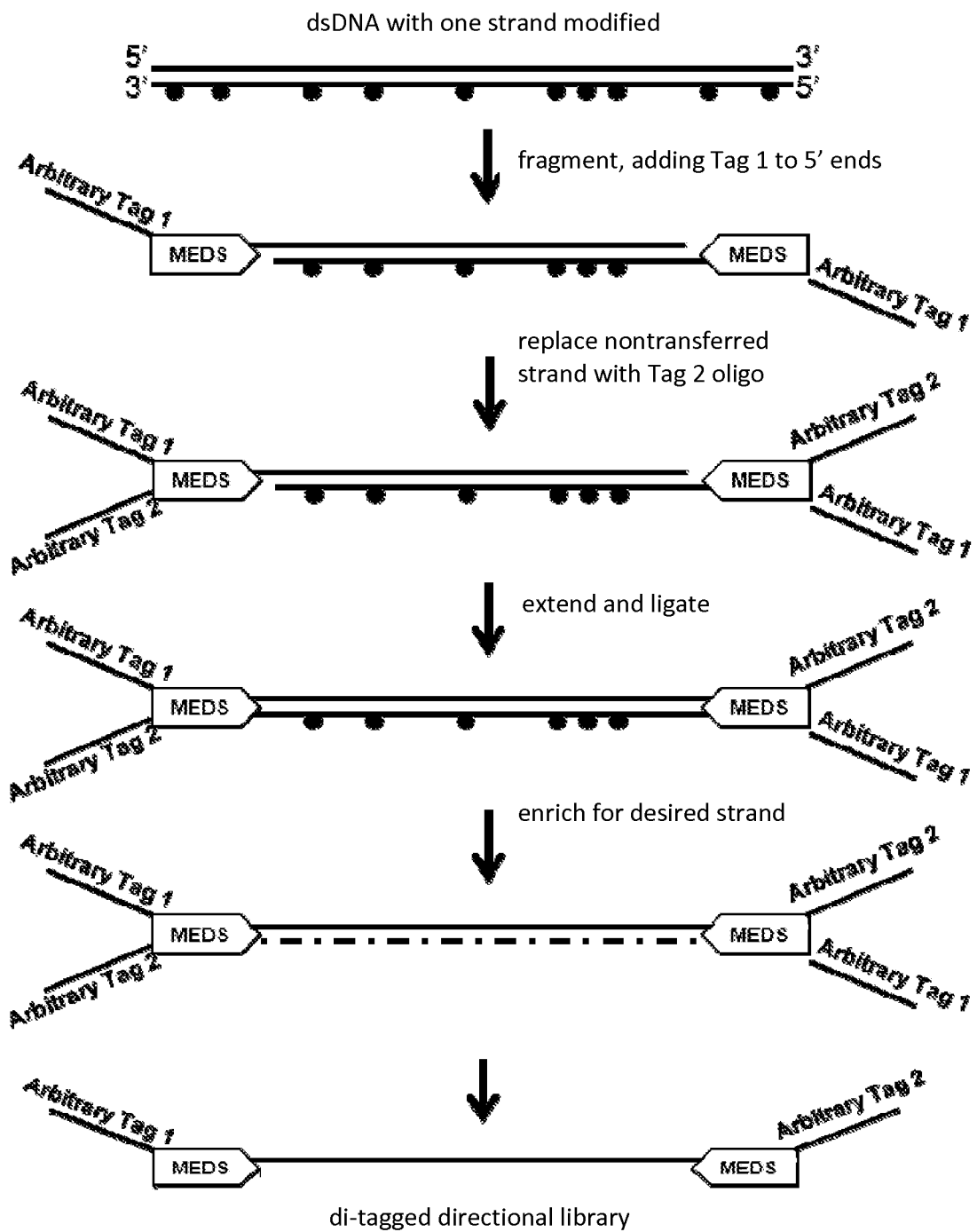
FIG. 5 illustrates a particular embodiment for generating a directional fragment product where the small circles in the dsDNA represent chemical modifications to the lower strand. In this diagram, the modified (lower) strand is considered the undesired strand. The result as shown is a product that preserves the desired (upper) strand, Arbitrary Tag 1 at the 5' end and Arbitrary Tag 2 at the 3' end.

The 14-base end sequence was selected for further experiments as illustrated in FIG. 4. After tagmentation with transposons having the 19-base transferred strand and the 14-base non-transferred strand, the product was mixed with replacement oligonucleotide (SEQ ID NO:19 with a sequencing tag as the "Arbitrary Tag 2") at 45° C. for 1 minute and then 37° C. for 30 minutes to remove the non-transferred and replace it with the replacement oligonucleotide. The remaining 9-base gaps were filled in using Tth polymerase, large fragment (without strand-displacement), followed by ligation using *E. coli* DNA ligase, according to manufacturer's recommended conditions.

Replacement was demonstrated by addition of an additional 100-base sequence as resolved on an Agilent BioAnalyzer 2100 using a DNA High-Sensitivity Chip. Genomic libraries of *Rhodobacter*, *E. coli*, and *Staphylococcus* were analyzed due to their divergent GC contents of 70, 50, and 33% respectively. These libraries were created utilizing oligonucleotide replacement strategies described here. The GC composition across the first 30 bases showed no additional insertion bias based on GC content of the host genome. Analysis of GC composition across the first 30 bases demonstrated no altered insertion bias based on GC content of the host genome. The data showed that there was an increased depth of coverage where the GC content is above 60% and consistent coverage at lower GC content ranges.

Example 2

Novel Transposase End Sequences

Several million Transposase end sequences were prepared using a partially randomized library based on the 19-base ME sequence (SEQ ID NO:3). From this library, a number of active transposon ends were identified using *E. coli* MG1655 genomic DNA as the target nucleic acid and sequenced on a Genome Analyzer$_{II}$ sequencing instrument (Illumina, Inc.).

```
                                              SEQ ID NO: 4
CGTTGTGTGGACGAGACAC  11G:C(C1)

SEQ ID NO: 5
CGTTGTGTGGACGAGACAG  11G:C(G1)

SEQ ID NO: 6
AGATGTGCATATGATACAG  Diff1(G1)

SEQ ID NO: 7
AG.TGT....AAGAGACAT  Shorty

SEQ ID NO: 22
TGACGCGGGTAAGAGACAA  Malt 1
```

```
                                              SEQ ID NO: 23
GGATGCGATGAGGAGACAA  Malt 6

SEQ ID NO: 24
ACATGACCAAGAGAGACAG  Malt 8

SEQ ID NO: 25
AGCGGTGAATAAGAGACAA  Malt 10

SEQ ID NO: 26
AGCGGTGAATAAGAGACAG  Malt 11

SEQ ID NO: 27
ACATGAGTATAAGAGACAA  Malt 12
```

The alternate end sequences were confirmed by capillary sequencing. One mutant designated 11G:C(G1) (SEQ ID NO:5) had a significantly high melting temperature (58° C. compared to 44° C.) and demonstrated comparable transposition activity in vitro as the ME sequence, as demonstrated by dilution in parallel with transposons with the ME sequence.

The above description discloses several methods and systems of the present invention. This invention is susceptible to modifications in the methods and materials, as well as alterations in the fabrication methods and equipment. Such modifications will become apparent to those skilled in the art from a consideration of this disclosure or practice of the invention disclosed herein. For example, the invention has been exemplified using nucleic acids but can be applied to other polymers as well. Consequently, it is not intended that this invention be limited to the specific embodiments disclosed herein, but that it cover all modifications and alternatives coming within the true scope and spirit of the invention.

All references cited herein including, but not limited to, published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

---

We claim:

1. A method for adding a tag to the double-stranded product of a tagmentation reaction, comprising the steps of:
   (a) providing a double-stranded target nucleic acid and a transposome having a transposase with two transposon end sequences: a "transferred strand" and a "non-transferred strand";
   (b) allowing the transposome to fragment the target nucleic acid, whereby the transferred strand is covalently transferred to a first strand of a fragment, and the non-transferred strand remains hybridized to the transferred strand;
   (c) removing the non-transferred strand from the transferred strand;
   (d) providing a replacement oligonucleotide that comprises a tag sequence, to hybridize to the transferred strand; and
   (e) ligating the replacement oligonucleotide to the second strand of the fragment;
   thereby generating a tagmentation product having a transferred strand and a replacement oligonucleotide.

2. The method of claim 1, wherein one strand of the target nucleic acid is chemically modified.

3. The method of claim 2, wherein the chemical modification is conversion of cytosines to uracils.

4. The method of claim 2, further comprising the step of
   (f) enriching for a desired strand.

5. The method of claim 4, wherein step (f) comprises treating the fragment with an enzyme that preferentially cleaves a nondesired strand of the fragment.

6. The method of claim 4, wherein step (f) is performed using a template-dependent polymerase that is sensitive to chemical modifications.

7. The method of claim 1, wherein the transposome comprises a Tn5 transposase.

8. The method of claim 1, wherein the transposome comprises a Mu transposase.

9. The method of claim 1, wherein the transferred strand comprises the ME sequence $$\text{MRWTGTGHWKAVGARACAV} \quad (\text{SEQ ID NO: 1})$$

or $$\text{NSHBGHSHDDRNGAKACAN}, \quad (\text{SEQ ID NO: 2})$$

but excluding $$\text{AGATGTGTATAAGAGACAG}. \quad (\text{SEQ ID NO: 3})$$

10. The method of claim 9, wherein the transferred strand further comprises a tag sequence.

11. The method of claim 1, wherein the non-transferred strand comprises $$\text{BTGTYTCBTN}_{1\text{-}10} \quad (\text{SEQ ID NO: 20})$$

or $$\text{NTGTMTCNTN}_{0\text{-}10}. \quad (\text{SEQ ID NO: 21})$$

12. The method of claim 1, wherein the non-transferred strand is selected from the group consisting of SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, and SEQ ID NO:18.

13. The method of claim 1, wherein step (e) further comprises an extension step.

* * * * *

SEQUENCE LISTING

<160> NUMBER OF SEQ ID NOS: 27

<210> SEQ ID NO 1
<211> LENGTH: 19
<212> TYPE: DNA
<213> ORGANISM: Artificial Sequence
<220> FEATURE:
<223> OTHER INFORMATION: synthetic construct

<400> SEQUENCE: 1
mrwtgtghwk avgaracav                                                19

<210> SEQ ID NO 2
<211> LENGTH: 19
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: n at position 1 may be A, C, T, or G
<220> FEATURE:
<221> NAME/KEY: misc_feature
<222> LOCATION: (12)..(12)
<223> OTHER INFORMATION: n at position 12 may be A, C, T, or G

```
<220> FEATURE:
<221> NAME/KEY: misc_feature
<222> LOCATION: (19)..(19)
<223> OTHER INFORMATION: n at position 19 may be A, C, T, or G

<400> SEQUENCE: 2
nshbghshdd rngakacan                                              19

<210> SEQ ID NO 3
<211> LENGTH: 19
<212> TYPE: DNA
<213> ORGANISM: Artificial Sequence
<220> FEATURE:
<223> OTHER INFORMATION: synthetic construct

<400> SEQUENCE: 3
agatgtgtat aagagacag                                              19

<210> SEQ ID NO 4
<211> LENGTH: 19
<212> TYPE: DNA
<213> ORGANISM: Artificial Sequence
<220> FEATURE:
<223> OTHER INFORMATION: synthetic construct

<400> SEQUENCE: 4
cgttgtgtgg acgagacac                                              19

<210> SEQ ID NO 5
<211> LENGTH: 19
<212> TYPE: DNA
<213> ORGANISM: Artificial Sequence
<220> FEATURE:
<223> OTHER INFORMATION: synthetic construct

<400> SEQUENCE: 5
cgttgtgtgg acgagacag                                              19

<210> SEQ ID NO 6
<211> LENGTH: 19
<212> TYPE: DNA
<213> ORGANISM: Artificial Sequence
<220> FEATURE:
<223> OTHER INFORMATION: synthetic construct

<400> SEQUENCE: 6
agatgtgcat atgatacag                                              19

<210> SEQ ID NO 7
<211> LENGTH: 14
<212> TYPE: DNA
<213> ORGANISM: Artificial Sequence
<220> FEATURE:
<223> OTHER INFORMATION: synthetic construct

<400> SEQUENCE: 7
agtgtaagag acat                                                   14

<210> SEQ ID NO 8
<211> LENGTH: 8
<212> TYPE: DNA
<213> ORGANISM: Artificial Sequence
<220> FEATURE:
<223> OTHER INFORMATION: synthetic construct

<400> SEQUENCE: 8
```

-continued

```
ctgtctct                                                        8

<210> SEQ ID NO 9
<211> LENGTH: 9
<212> TYPE: DNA
<213> ORGANISM: Artificial Sequence
<220> FEATURE:
<223> OTHER INFORMATION: synthetic construct

<400> SEQUENCE: 9 ctgtctctt                                                       9

<210> SEQ ID NO 10
<211> LENGTH: 10
<212> TYPE: DNA
<213> ORGANISM: Artificial Sequence
<220> FEATURE:
<223> OTHER INFORMATION: synthetic construct

<400> SEQUENCE: 10
ctgtctctta                                                     10

<210> SEQ ID NO 11
<211> LENGTH: 11
<212> TYPE: DNA
<213> ORGANISM: Artificial Sequence
<220> FEATURE:
<223> OTHER INFORMATION: synthetic construct

<400> SEQUENCE: 11
ctgtctctta t                                                   11

<210> SEQ ID NO 12
<211> LENGTH: 12
<212> TYPE: DNA
<213> ORGANISM: Artificial Sequence
<220> FEATURE:
<223> OTHER INFORMATION: synthetic construct

<400> SEQUENCE: 12
ctgtctctta ta                                                  12

<210> SEQ ID NO 13
<211> LENGTH: 13
<212> TYPE: DNA
<213> ORGANISM: Artificial Sequence
<220> FEATURE:
<223> OTHER INFORMATION: synthetic construct

<400> SEQUENCE: 13
ctgtctctta tac                                                 13

<210> SEQ ID NO 14
<211> LENGTH: 14
<212> TYPE: DNA
<213> ORGANISM: Artificial Sequence
<220> FEATURE:
<223> OTHER INFORMATION: synthetic construct

<400> SEQUENCE: 14
ctgtctctta taca                                                14

<210> SEQ ID NO 15
<211> LENGTH: 15
<212> TYPE: DNA
<213> ORGANISM: Artificial Sequence
```

```
<220> FEATURE:
<223> OTHER INFORMATION: synthetic construct

<400> SEQUENCE: 15
ctgtctctta tacac                                                        15

<210> SEQ ID NO 16
<211> LENGTH: 16
<212> TYPE: DNA
<213> ORGANISM: Artificial Sequence
<220> FEATURE:
<223> OTHER INFORMATION: synthetic construct

<400> SEQUENCE: 16
ctgtctctta tacaca                                                       16

<210> SEQ ID NO 17
<211> LENGTH: 17
<212> TYPE: DNA
<213> ORGANISM: Artificial Sequence
<220> FEATURE:
<223> OTHER INFORMATION: synthetic construct

<400> SEQUENCE: 17
ctgtctctta tacacat                                                      17

<210> SEQ ID NO 18
<211> LENGTH: 18
<212> TYPE: DNA
<213> ORGANISM: Artificial Sequence
<220> FEATURE:
<223> OTHER INFORMATION: synthetic construct

<400> SEQUENCE: 18
ctgtctctta tacacatc                                                     18

<210> SEQ ID NO 19
<211> LENGTH: 19
<212> TYPE: DNA
<213> ORGANISM: Artificial Sequence
<220> FEATURE:
<223> OTHER INFORMATION: synthetic construct

<400> SEQUENCE: 19
ctgtctctta tacacatct                                                    19

<210> SEQ ID NO 20
<211> LENGTH: 19
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (10)..(19)
<223> OTHER INFORMATION: n at positions 10-19 may be A, C, T, or G and
      up to nine of them may be absent

<400> SEQUENCE: 20
btgtytcbtn nnnnnnnnn                                                    19

<210> SEQ ID NO 21
<211> LENGTH: 19
<212> TYPE: DNA
<213> ORGANISM: Artificial Sequence
<220> FEATURE:
<223> OTHER INFORMATION: synthetic construct
```

```
<220> FEATURE:
<221> NAME/KEY: misc_feature
<222> LOCATION: (1)..(1)
<223> OTHER INFORMATION: n at position 1 may be A, C, T, or G
<220> FEATURE:
<221> NAME/KEY: misc_feature
<222> LOCATION: (8)..(8)
<223> OTHER INFORMATION: n at position 8 may be A, C, T, or G
<220> FEATURE:
<221> NAME/KEY: misc_feature
<222> LOCATION: (10)..(19)
<223> OTHER INFORMATION: n at position 8 may be A, C, T, or G and up to
      9 of them may be absent

<400> SEQUENCE: 21
ntgtmtcntn nnnnnnnnn                                                  19

<210> SEQ ID NO 22
<211> LENGTH: 19
<212> TYPE: DNA
<213> ORGANISM: Artificial Sequence
<220> FEATURE:
<223> OTHER INFORMATION: synthetic construct

<400> SEQUENCE: 22
tgacgcgggt aagagacaa                                                  19

<210> SEQ ID NO 23
<211> LENGTH: 19
<212> TYPE: DNA
<213> ORGANISM: Artificial Sequence
<220> FEATURE:
<223> OTHER INFORMATION: synthetic construct

<400> SEQUENCE: 23
ggatgcgatg aggagacaa                                                  19

<210> SEQ ID NO 24
<211> LENGTH: 19
<212> TYPE: DNA
<213> ORGANISM: Artificial Sequence
<220> FEATURE:
<223> OTHER INFORMATION: synthetic construct

<400> SEQUENCE: 24
acatgaccaa gagagacag                                                  19

<210> SEQ ID NO 25
<211> LENGTH: 19
<212> TYPE: DNA
<213> ORGANISM: Artificial Sequence
<220> FEATURE:
<223> OTHER INFORMATION: synthetic construct

<400> SEQUENCE: 25
agcggtgaat aagagacaa                                                  19

<210> SEQ ID NO 26
<211> LENGTH: 19
<212> TYPE: DNA
<213> ORGANISM: Artificial Sequence
<220> FEATURE:
<223> OTHER INFORMATION: synthetic construct

<400> SEQUENCE: 26
agcggtgaat aagagacag                                                  19
```

```
<210> SEQ ID NO 27
<211> LENGTH: 19
<212> TYPE: DNA
<213> ORGANISM: Artificial Sequence
<220> FEATURE:
<223> OTHER INFORMATION: synthetic construct

<400> SEQUENCE: 27
acatgagtat aagagacaa                                                  19
```